(12) United States Patent
Zanardi et al.

(10) Patent No.: US 10,912,747 B2
(45) Date of Patent: Feb. 9, 2021

(54) ANTIMICROBIAL COMPOSITION

(71) Applicant: Rottapharm SpA, Milan (IT)

(72) Inventors: Andrea Zanardi, Milan (IT); Alessandra Cercaci, Rivalta di Torino (IT); Ivan Montaldo, Castagnito (IT); Joachim Maus, Muhlheim (DE)

(73) Assignee: Rottapharm SpA

( * ) Notice: Subject to any disclaimer, the term of this patent is extended or adjusted under 35 U.S.C. 154(b) by 0 days.

(21) Appl. No.: 16/329,421

(22) PCT Filed: Sep. 4, 2017

(86) PCT No.: PCT/EP2017/072127
§ 371 (c)(1),
(2) Date: Feb. 28, 2019

(87) PCT Pub. No.: WO2018/046448
PCT Pub. Date: Mar. 15, 2018

(65) Prior Publication Data
US 2019/0247341 A1    Aug. 15, 2019

(30) Foreign Application Priority Data
Sep. 7, 2016  (EP) .................................. 16001946

(51) Int. Cl.
| | | |
|---|---|---|
| *A61K 31/19* | (2006.01) | |
| *A01N 31/02* | (2006.01) | |
| *A01N 37/36* | (2006.01) | |
| *A61K 31/047* | (2006.01) | |
| *A61K 31/17* | (2006.01) | |
| *A61K 9/00* | (2006.01) | |
| *A61K 47/10* | (2017.01) | |
| *A61K 47/12* | (2006.01) | |
| *A61K 8/34* | (2006.01) | |
| *A61Q 19/10* | (2006.01) | |
| *A61Q 17/00* | (2006.01) | |
| *A61K 8/365* | (2006.01) | |
| *A61P 31/10* | (2006.01) | |

(52) U.S. Cl.
CPC .............. *A61K 31/19* (2013.01); *A01N 31/02* (2013.01); *A01N 37/36* (2013.01); *A61K 8/345* (2013.01); *A61K 8/365* (2013.01); *A61K 9/0014* (2013.01); *A61K 31/047* (2013.01); *A61K 31/17* (2013.01); *A61K 47/10* (2013.01); *A61K 47/12* (2013.01); *A61P 31/10* (2018.01); *A61Q 17/005* (2013.01); *A61Q 19/10* (2013.01)

(58) Field of Classification Search
None
See application file for complete search history.

(56) References Cited

U.S. PATENT DOCUMENTS

| 7,074,832 B2 * | 7/2006 | Bhagwat ................ A61K 8/466 514/588 |
|---|---|---|
| 2005/0222276 A1 | 10/2005 | Schmaus |
| 2009/0175806 A1 * | 7/2009 | Modak .................... A61K 8/365 424/58 |
| 2012/0201902 A1 * | 8/2012 | Modak .................... A01N 31/02 424/618 |

FOREIGN PATENT DOCUMENTS

| EP | 1598064 A1 | 11/2005 |
|---|---|---|
| WO | 9611572 A1 | 4/1996 |
| WO | 2008046796 A2 | 4/2008 |
| WO | 2008119841 A2 | 10/2008 |
| WO | 2011117126 A2 | 9/2011 |

OTHER PUBLICATIONS

Yamarik et al (Int J Toixol 24:1-56, 2005) (Year: 2005).*
Nature's Gift Aromatherapy Products (available online at https://www.naturesgift.com/aromatherapy-information/what-is-aromatherapy/hydrosols/ with attached attached Internet Archive Report) (Year: 2016).*
PCT International Search Report for application PCT/EP2017/072127, dated Mar. 15, 2018, 4 pages.
Written Opinion of the International Searching Authority for PCT/EP2017/072127, dated Mar. 15, 2018, 6 pages.

* cited by examiner

*Primary Examiner* — Craig D Ricci

(57) ABSTRACT

The invention relates to a composition having antimicrobial and hygroscopic properties and the composition comprises a carboxylic acid compound as well as at least one C3-C6 diol and at least one C8-C12 diol. The composition of the invention may be used for cleansing, disinfection, surface treatment, impregnation and for antimicrobial treatment. The composition is particularly useful for treatment of fungal infections of the nail (onychomycosis).

4 Claims, No Drawings

ANTIMICROBIAL COMPOSITION

CROSS-REFERENCE TO RELATED APPLICATIONS

This application is a U.S. national stage filing under 35 U.S.C. § 371 of International Patent Application PCT/EP2017/072127, filed on Sep. 4, 2017, which claims the benefit of the filing date of European Patent Application EP 16001946.9, filed on Sep. 7, 2016. The contents of each of the preceding are hereby incorporated by reference in their entities.

The invention relates to a composition and its use as antimicrobial agent with hygroscopic properties. The composition comprises a carboxylic acid compound as well as at least one C3-C6 diol and at least one C8-C12 diol. Carboxylic acid compounds in accordance with the present invention are carboxylic acids or salts thereof, having up to 10 carbon atoms. The composition of the invention may be used for cleansing, disinfection, surface treatment, impregnation and for antimicrobial treatment. The composition is particularly useful for treatment of fungal infections of the nail (onychomycosis).

BACKGROUND OF THE INVENTION

Compositions used for cleansing, disinfection, surface treatment, impregnation and for antimicrobial treatment are known from the prior art.

WO 96/11572 A1 discloses a composition having antimicrobial and hygroscopic properties comprising carboxylic acids having up to 10 carbon atoms and the salts thereof as well as C3-C10 diols as a mixture, or as a chemical compound in the form of an ester, polyester or polymer. It is described that an increased antimicrobial effect was obtained by a combination of diols and carboxylic acids. It is also disclosed that the compositions may comprise mixtures of several carboxylic acids and diols, wherein diols having shorter carbon chains serve as solvents for diols having longer chains. However, even though WO 96/11572 A1 discloses that the compositions may comprise mixtures of shorter and longer diols, a composition comprising at least one C3-C6 diol and at least one C8-C12 diol is not disclosed. Rather, WO 96/11572 A1 discloses that C3-C6 diols are preferred over C7-C10 diols. In fact, none of the examples comprises any C7-C10 diols. Examples comprising more than one diol comprise propylene glycol (C3) and hexylene glycol (C6). Thus, mixtures of shorter and longer diols in the sense of WO 96/11572 A1 are to be understood as mixtures of C3 glycols and C6 glycols. The amount of C7-C10 diols according to WO 96/11572 A1 is far above 0.1 to 1% by weight.

In view of WO 2012/107565 A1 it appears that there was a long-lasting prejudice in the art against the use of diols having more than 6 carbon atoms in antifungal compositions. WO 2012/107565 A1 discloses a pharmaceutical composition for the treatment of fungal infection of the nail comprising an antifungal allylamine compound present in an amount of about 10%, an organic acid or an ester thereof, a diol and a sequestering agent. Suitable diols are disclosed to be propanediol, butanediol, pentanediol, and hexanediol, wherein propanediol and butanediol are particularly suitable. Mixtures of the mentioned diols are also suitable. It is disclosed that pentanediol seems to have the same effect on the penetration of the composition into the nail as propanediol which performs better than hexanediol from a penetration point of view. Thus, it seems that penetration of the composition into the nail is impaired when too long diols, in particular diols with 6 carbon atoms and more, are used. This explains why shorter diols were so far preferred in the art.

Even though compositions for cleansing, disinfection, surface treatment, impregnation and for antimicrobial treatment are known from the prior art, these compositions are often not optimal with regard to their antimicrobial effect, in particular on fungi. However, compositions with improved effects would be desirable in order to enable more effective cleansing, disinfection, surface treatment, impregnation and antimicrobial treatment.

DESCRIPTION OF THE INVENTION

Said problems are solved by the subject-matter of the patent claims. The problems are in particular solved by a composition comprising carboxylic acids or salts thereof, having up to 10 carbon atoms, wherein the composition further comprises at least one first diol having from 3 to 6 carbon atoms and at least one second diol having from 8 to 12 carbon atoms. The composition has an increased antimicrobial effect and a wide antimicrobial spectrum having great inhibitory effect on several Dermatophytes, yeast fungi, mould fungi, bacteria and viruses. In particular, the antimicrobial effect on fungi is extraordinarily increased in comparison to prior art compositions. The composition of the invention is furthermore kind to the skin, environmentally friendly, low allergenic, keratolytic active and has also a hygroscopic effect and does not evaporate as fast as e.g. ethanol. From the research carried out by the inventors in developing the invention an increased antimicrobial effect was obtained by a combination of at least one C3-C6 diol with at least one C8-C12 diol. Preferably, the composition comprises a C3 diol, in particular propylene glycol, and a C10 diol, in particular decylene glycol.

According to the present description the term "CX diol" corresponds to a diol having exactly X carbon atoms. Thus, for example a C3 diol is to be understood as a diol having exactly 3 carbon atoms, whereas a C10 diol is to be understood as a diol having exactly 10 carbon atoms. The term "C3-C6 diol" describes diols having from 3 to 6 carbon atoms and the term "C8-C12 diol" describes diols having from 8 to 12 carbon atoms.

Preferably, the first diol is a diol selected from the group consisting of propylene glycol, butylene glycol, pentylene glycol and hexylene glycol. More preferably, the first diol has 3 or 4 carbon atoms. More preferred, the first diol is propylene glycol, butylene glycol or mixtures thereof.

More preferred, the first diol has exactly 3 carbon atoms. Particularly preferred, the first diol is propylene glycol.

Preferably, the second diol is a diol selected from the group consisting of octylene glycol, nonylene glycol, decylene glycol, undecylene glycol and dodecylene glycol. More preferred, the second diol has exactly 10 carbon atoms. Even more preferred, the second diol is decylene glycol. For the second diol the antibacterial activity as well as the intrinsic toxicity to fungus decreases in case the number of carbon atoms becomes too high. If the number of carbon atoms is too low undesired osmoses will appear.

In addition to the first and second diol, the composition of the present invention may optionally comprise further diols that do not have from 3 to 6 carbon atoms or from 8 to 12 carbon atoms. For example, the composition may comprise a diol having 7 carbon atoms, in particular heptylene glycol.

Diols are mainly identified by their trivial names in the present description such as for example propylene glycol or decylene glycol. The systematic names of such compounds as described herein are summarized in the following table 1:

TABLE 1

| Trivial name | Systematic name |
| --- | --- |
| Propylene glycol | 1,2-propane diol |
| Butylene glycol | 1,3-butane diol |
| Pentylene glycol | 1,2-pentylene diol |
| Hexylene glycol | 2-methyl-2,4-pentane diol |
| Heptylene glycol | 1,2-heptylene diol |
| Octylene glycol | 1,2-octylene diol |
| Nonylene glycol | 1,2-nonylene diol |
| Decylene glycol | 1,2-decylene diol |
| Undecylene glycol | 1,2-undecylene diol |
| Dodecylene glycol | 1,2-dodecylene diol |

In case that the diol compound can have stereoisomers usually the racemic species is used according to the present invention. However, the skilled person will make use of R- and/or S-forms as well in case this option appears suitable.

The term carboxylic acids having up to 10 carbon atoms, which may be used according to the invention, relates to saturated or unsaturated, straight or branched aliphatic mono-, di- or polycarboxylic acids having up to 10 carbon atoms, including araliphatic or aromatic dicarboxylic acids, oxy or hydroxy carboxylic acids having up to 8 carbon atoms. Such carboxylic acids having up to 10 carbon atoms or salts of such carboxylic acids, are also referred to as "carboxylic acid compounds" according to the present description. Preferred carboxylic acids are selected from the group consisting of formic acid, acetic acid, propionic acid, butyric acid, valeric acid, caproic acid, caprylic acid, capric acid, sorbic acid, oxalic acid, malonic acid, fumaric acid, succinic acid, glutaric acid, adipic acid, pimelic acid, oxalacetic acid, phtalic acid, glycolic acid, citric acid, lactic acid, glucuronic acid, glyceric acid, malic acid, tartaric acid, tartronic acid, hydroxibutyric acid, hydroxipropionic acid, pyruvic acid and mixtures thereof. More preferred, the carboxylic acid is selected from the group consisting of acetic acid, citric acid, tartaric acid, lactic acid and mixtures thereof. Even more preferred, the carboxylic acid is lactic acid.

The composition according to the invention may contain additives such as water, C1-C8 alcohols, oils preferably vegetable oils such as peanut oil, olive oil, rape seed oil, linseed oil, tall oil and castor oil with or without being combined with emulsifying agents. Also surfactants may be added to strengthen the cleansing effects. Urea and/or polyethylene glycol may also be included. Furthermore, the composition may comprise bases such as KOH and/or NaOH for adjustment of the pH of the composition. The composition may also comprise one or more hydrolates, for example mint hydrolate, oregano hydrolate, thymus hydrolate or mixtures thereof as described in more detail below.

Other additives in accordance with the invention may be antimycotics, preferably azole derivatives, allyl amines and amorolfine; antiviral agents, preferable idoxyuridine, acyclovir, phosphonio formic acid, podophyllotoxin; antibacterial agents such as biguanides and amidinesquinolines, benzoyl peroxide, bibrocatole, clindamycin, neomycin, fucidinic acid, mupirocin, sulphur; glucocorticoides, preferably hydrocortisone and flouro substituted steroids, gels and enzymes.

The composition of the invention may be liquid or gel-like. In order to obtain gel-like properties, the composition of the invention may comprise one or more gelling agents. Preferred gelling agent are polyquaterniums, in particular polyquaternium-10, which is quaternized hydroxyethyl cellulose, thus the quaternary trimethylammonium salt of hydroxyethyl cellulose.

As described above, the composition of the present invention comprises at least one carboxylic acid compound, at least one C3-C6 diol and at least one C8-C12 diol. In preferred embodiments, the composition comprises exactly one carboxylic acid compound, exactly one C3-C6 diol and exactly one C8-C12 diol. In alternative embodiments, the composition of the invention comprises two or more carboxylic acid compounds, two or more C3-C6 diols and two or more C8-C12 diols.

The amounts of certain components indicated in the present description correspond to the total amount of this component in the compositions of the invention if not indicated otherwise. For example, if it is said in the present description that the composition comprises C3-C6 diol in a certain amount, this indicates the total amount of C3-C6 diol in the composition. For example, a total amount of C3-C6 diol of 60 percent by weight may mean that the composition comprises 40 percent by weight of propylene glycol and 20 percent by weight of butylene glycol or that the composition comprises 60 percent by weight of propylene glycol. The same holds true for all components of the composition of the present invention identified by collective terms such as carboxylic acid or carboxylic acid compound, C8-C12 diol, base, hydrolates and others.

Preferably, the composition comprises carboxylic acid compound in an amount of 2 to 30 percent by weight, C3-C6 diol in an amount of 50 to 90 percent by weight and C8-C12 diol in an amount of from 0.1 to 10 percent by weight. More preferably, the composition comprises carboxylic acid compound in an amount of 5 to 20 percent by weight, C3-C6 diol in an amount of 60 to 80 percent by weight and C8-C12 diol in an amount of from 0.5 to 2 percent by weight. Even more preferably, the composition comprises carboxylic acid compound in an amount of 6 to 12 percent by weight, C3-C6 diol in an amount of 65 to 75 percent by weight and C8-C12 diol in an amount of from 0.6 to 1.5 percent by weight.

Carboxylic acid compounds impair fungal growth by lowering the pH value. Preferably, the composition comprises carboxylic acid compound in an amount of at least 1 percent by weight, more preferably at least 2 percent by weight, more preferably at least 4 percent by weight, more preferably at least 5 percent by weight, more preferably at least 6 percent by weight, more preferably at least 7 percent by weight, more preferably at least 7.5 percent by weight. If the amount of carboxylic acid compound is too low, the achieved effect may be impaired. If the amount of carboxylic acid compound is too high, the costs will be too high as well. Preferably, the composition comprises carboxylic acid compound in an amount of at most 35 percent by weight, more preferably at most 30 percent by weight, more preferably at most 25 percent by weight, more preferably at most 20 percent by weight, more preferably at most 15 percent by weight, more preferably at most 12 percent by weight, more preferably at most 10 percent by weight, more preferably at most 9 percent by weight. Preferably, the composition comprises carboxylic acid compound in an amount of from 1 to 35 percent by weight, more preferably from 2 to 30 percent by weight, more preferably from 4 to 25 percent by weight, more preferably from 5 to 20 percent by weight, more preferably from 6 to 15 percent by weight, more preferably from 7 to 12 percent by weight, more preferably from 7.5 to 10 percent by weight. In another preferred embodiment, the composition preferably comprises carboxylic acid compound in an amount of from 7 to 9 percent by weight.

A preferred amount is in the range of 1% weight based on the total composition.

C3-C6 glycol has hydrating properties due to its water-binding capability. Preferably, the composition comprises C3-C6 diol in an amount of at least 40 percent by weight, more preferably at least 45 percent by weight, more preferably at least 50 percent by weight, more preferably at least 55 percent by weight, more preferably at least 60 percent by weight, more preferably at least 65 percent by weight, more preferably at least 67 percent by weight. If the amount of C3-C6 glycol is too low, the achieved effect may be impaired. Preferably, the composition comprises C3-C6 diol in an amount of at most 98 percent by weight, more preferably at most 95 percent by weight, more preferably at most 90 percent by weight, more preferably at most 85 percent by weight, more preferably at most 80 percent by weight, more preferably at most 75 percent by weight, more preferably at most 70 percent by weight. Preferably, the composition comprises C3-C6 diol in an amount of from 40 to 98 percent by weight, more preferably from 45 to 95 percent by weight, more preferably from 50 to 90 percent by weight, more preferably from 55 to 85 percent by weight, more preferably from 60 to 80 percent by weight, more preferably from 65 to 75 percent by weight, more preferably from 67 to 70 percent by weight.

C8-C12 diols are able to bind water and potentially impair fungal diffusion by an osmotic mechanism. Preferably, the composition comprises C8-C12 diol in an amount of at least 0.1 percent by weight, more preferably at least 0.2 percent by weight, more preferably at least 0.4 percent by weight, more preferably at least 0.5 percent by weight, more preferably at least 0.6 percent by weight, more preferably at least 0.7 percent by weight, more preferably at least 0.8 percent by weight. If the amount of C8-C12 glycol is too low, the achieved effect may be impaired. Preferably, the composition comprises C8-C12 diol in an amount of at most 10 percent by weight, more preferably at most 5 percent by weight, more preferably at most 4 percent by weight, more preferably at most 2 percent by weight, more preferably at most 1.5 percent by weight, more preferably at most 1.2 percent by weight, more preferably at most 1.1 percent by weight. Preferably, the composition comprises C8-C12 diol in an amount of from 0.1 to 10 percent by weight, more preferably from 0.2 to 5 percent by weight, more preferably from 0.4 to 4 percent by weight, more preferably from 0.5 to 2 percent by weight, more preferably from 0.6 to 1.5 percent by weight, more preferably from 0.7 to 1.2 percent by weight, more preferably from 0.8 to 1.1 percent by weight. In another preferred embodiment, the composition comprises C8-C12 diol in an amount of from 0.8 to 1.2 percent by weight.

Preferably, the mass ratio of the amount of C3-C6 diol in the composition and the amount of C8-C12 diol in the composition (C3-C6 diol:C8-C12 diol) is at least 10:1, more preferably at least 20:1, more preferably at least 30:1, more preferably at least 40:1, more preferably at least 50:1, more preferably at least 60:1, more preferably at least 65:1. Preferably, the mass ratio of the amount of C3-C6 diol in the composition and the amount of C8-C12 diol in the composition (C3-C6 diol:C8-C12 diol) is at most 150:1, more preferably at most 120:1, more preferably at most 100:1, more preferably at most 90:1, more preferably at most 80:1, more preferably at most 75:1, more preferably at most 70:1. Preferably, the mass ratio of the amount of C3-C6 diol in the composition and the amount of C8-C12 diol in the composition (C3-C6 diol:C8-C12 diol) is in the range from 10:1 to 150:1, more preferably from 20:1 to 120:1, more preferably from 30:1 to 100:1, more preferably from 40:1 to 90:1, more preferably from 50:1 to 80:1, more preferably from 60:1 to 75:1, more preferably from 65:1 to 70:1.

Preferably, the mass ratio of the amount of C3-C6 diol in the composition and the amount of carboxylic acid compound in the composition (C3-C6 diol:carboxylic acid compound) is at least 1:1, more preferably at least 2:1, more preferably at least 3:1, more preferably at least 4:1, more preferably at least 5:1, more preferably at least 6:1, more preferably at least 7:1. Preferably, the mass ratio of the amount of C3-C6 diol in the composition and the amount of carboxylic acid compound in the composition (C3-C6 diol:carboxylic acid compound) is at most 25:1, more preferably at most 20:1, more preferably at most 15:1, more preferably at most 12:1, more preferably at most 11:1, more preferably at most 10:1, more preferably at most 9:1. Preferably, the mass ratio of the amount of C3-C6 diol in the composition and the amount of carboxylic acid compound in the composition (C3-C6 diol:carboxylic acid compound) is in the range from 1:1 to 25:1, more preferably from 2:1 to 20:1, more preferably from 3:1 to 15:1, more preferably from 4:1 to 12:1, more preferably from 5:1 to 11:1, more preferably from 6:1 to 10:1, more preferably from 7:1 to 9:1.

Preferably, the mass ratio of the amount of carboxylic acid compound in the composition and the amount of C8-C12 diol in the composition (carboxylic acid compound:C8-C12 diol) is at least 1:1, more preferably at least 2:1, more preferably at least 3:1, more preferably at least 4:1, more preferably at least 5:1, more preferably at least 6:1, more preferably at least 7:1. Preferably, the mass ratio of the amount of carboxylic acid compound in the composition and the amount of C8-C12 diol in the composition (carboxylic acid compound:C8-C12 diol) is at most 30:1, more preferably at most 25:1, more preferably at most 20:1, more preferably at most 15:1, more preferably at most 12:1, more preferably at most 11:1, more preferably at most 10:1. Preferably, the mass ratio of the amount of carboxylic acid compound in the composition and the amount of C8-C12 diol in the composition (carboxylic acid compound:C8-C12 diol) is in the range from 1:1 to 30:1, more preferably from 2:1 to 25:1, more preferably from 3:1 to 20:1, more preferably from 4:1 to 15:1, more preferably from 5:1 to 12:1, more preferably from 6:1 to 11:1, more preferably from 7:1 to 10:1.

Urea has a hydrating effect due to its keratolytic and softening properties. Preferably, the composition of the present invention comprises urea. The amount of urea should not be below a certain threshold because then the nail will not be softened in case of onychomycosis treatment and the diols cannot pass the natural barrier of the nail. Preferably, the composition comprises urea in an amount of at least 2 percent by weight, more preferably at least 4 percent by weight, more preferably at least 8 percent by weight, more preferably at least 10 percent by weight, more preferably at least 12 percent by weight, more preferably at least 14 percent by weight, more preferably at least 15 percent by weight, more preferably at least 16 percent by weight. If the amount of urea is too low, the achieved effect may be impaired. Preferably, the composition comprises urea in an amount of at most 50 percent by weight, more preferably at most 45 percent by weight, more preferably at most 40 percent by weight, more preferably at most 35 percent by weight, more preferably at most 30 percent by weight, more preferably at most 25 percent by weight, more preferably at most 22 percent by weight, more preferably at most 21 percent by weight. Preferably, the composition comprises urea in an amount of from 2 to 50 percent by weight, more preferably from 4 to 45 percent by weight, more preferably from 8 to 40 percent by weight, more preferably from 10 to 35 percent by weight, more preferably from 12 to 30 percent by weight, more preferably from 14 to 25 percent by weight, more preferably from 16 to 22 percent by weight. In another preferred embodiment, the composition comprises urea in an amount from 15 to 21 percent by weight.

Preferably, the composition of the present invention comprises a base such as NaOH or KOH. A base is advantageous for adjusting the pH of the composition. Preferably, the composition comprises base in an amount of at least 0.1 percent by weight, more preferably at least 0.2 percent by weight, more preferably at least 0.4 percent by weight, more preferably at least 0.5 percent by weight, more preferably at least 0.6 percent by weight, more preferably at least 0.7 percent by weight, more preferably at least 0.8 percent by weight. If the amount of base is too low, the pH value of the composition may be very low, which may impair the achieved effects. Preferably, the composition comprises base in an amount of at most 10 percent by weight, more preferably at most 5 percent by weight, more preferably at most 4 percent by weight, more preferably at most 2 percent by weight, more preferably at most 1.5 percent by weight, more preferably at most 1.2 percent by weight, more preferably at most 1.1 percent by weight. If the amount of base is too high, the pH value of the composition may be very high, which may impair the achieved effects. Preferably, the composition comprises base in an amount of from 0.1 to 10 percent by weight, more preferably from 0.2 to 5 percent by weight, more preferably from 0.4 to 4 percent by weight, more preferably from 0.5 to 2 percent by weight, more preferably from 0.6 to 1.5 percent by weight, more preferably from 0.7 to 1.2 percent by weight, more preferably from 0.8 to 1.1 percent by weight.

Preferably, the composition comprises one more hydrolates. More preferably, the composition comprises exactly one hydrolate. Hydrolates are also known as herbal distillates, floral waters, hydrosols, herbal waters or essential waters. Hydrolates usually comprise essential oils and/or water-soluble components obtained by distillation of plants or herbs. Preferred hydrolates in accordance with the present invention are selected from the group consisting of mint hydrolate, oregano hydrolate, thymus hydrolate and mixtures thereof. Mint hydrolate is particularly preferred. It was surprisingly found by the present inventors that hydrolates further improve the antimicrobial effect of the compositions of the present invention. Therefore, the composition of the invention preferably comprises hydrolates in an amount of at least 0.01 percent by weight, more preferably at least 0.02 percent by weight, more preferably at least 0.04 percent by weight, more preferably at least 0.05 percent by weight, more preferably at least 0.06 percent by weight, more preferably at least 0.07 percent by weight, more preferably at least 0.08 percent by weight. The present inventors found that hydrolates may improve the storability of the compositions of the invention. If the amount of hydrolates is too low, the storability of the compositions may be impaired. Preferably, the composition comprises hydrolates in an amount of at most 1 percent by weight, more preferably at most 0.5 percent by weight, more preferably at most 0.4 percent by weight, more preferably at most 0.2 percent by weight, more preferably at most 0.15 percent by weight, more preferably at most 0.12 percent by weight, more preferably at most 0.11 percent by weight. Preferably, the composition comprises hydrolates in an amount of from 0.01 to 1 percent by weight, more preferably from 0.02 to 0.5 percent by weight, more preferably from 0.04 to 0.4 percent by weight, more preferably from 0.05 to 0.2 percent by weight, more preferably from 0.06 to 0.15 percent by weight, more preferably from 0.07 to 0.12 percent by weight, more preferably from 0.08 to 0.11 percent by weight.

In a particularly preferred embodiment, the composition of the present invention comprises at least one carboxylic acid compound, at least one C3-C6 diol, at least one C8-C12 diol, urea, a base, in particular NaOH, and one or more hydrolate. In an even more preferred embodiment, the composition of the invention comprises exactly one carboxylic acid compound, exactly one C3-C6 diol, exactly one C8-C12 diol, urea, a base, in particular NaOH, and exactly one hydrolate selected from the group consisting of mint hydrolate, oregano hydrolate and thymus hydrolate. In an even more preferred embodiment, the composition of the invention comprises exactly one carboxylic acid compound, exactly one C3-C6 diol, exactly one C8-C12 diol, urea, a base, in particular NaOH, and mint hydrolate.

Preferably, the compositions of the present invention have a pH of at least 1.5, more preferably at least 2.0, more preferably at least 2.5, more preferably, at least 3.0, more preferably at least 3.5. Preferably, the compositions of the invention have a pH of at most 6.5, more preferably at most 6.0, more preferably at most 5.5, more preferably at most 5.0, more preferably at most 4.5. Preferably, the pH of the compositions of the invention is from 1.5 to 6.5, more preferably from 2.0 to 6.0, more preferably from 2.5 to 5.5, more preferably from 3.0 to 5.0, more preferably from 3.5 to 4.5. If the pH is too high or too low, the achieved effects may be impaired. A very preferred pH is in the range of 5, which allows softening of the nail in the case of onychomycosis treatment.

In a preferred embodiment, the composition of the invention comprises the following components in percent by weight:

| Component | Amount (percent by weight) |
| --- | --- |
| C3-C6 diol | 50 to 90 |
| C8-C12 diol | 0.1 to 10 |
| Urea | 4 to 45 |
| Carboxylic acid compound | 2 to 30 |
| Base | 0.1 to 10 |

More preferred, the composition of the invention comprises the following components in percent by weight:

| Component | Amount (percent by weight) |
| --- | --- |
| C3-C6 diol | 60 to 80 |
| C8-C12 diol | 0.4 to 4 |
| Urea | 10 to 35 |
| Carboxylic acid compound | 5 to 20 |
| Base | 0.4 to 4 |

Even more preferred, the composition of the invention comprises the following components in percent by weight:

| Component | Amount (percent by weight) |
| --- | --- |
| C3-C6 diol | 65 to 75 |
| C8-C12 diol | 0.6 to 1.5 |
| Urea | 14 to 25 |
| Carboxylic acid compound | 6 to 15 |
| Base | 0.6 to 1.5 |

The composition of the present invention may also comprise one or more hydrolates as described above. In such an embodiment, the composition of the invention preferably comprises the following components in percent by weight:

| Component | Amount (percent by weight) |
| --- | --- |
| C3-C6 diol | 50 to 90 |
| C8-C12 diol | 0.1 to 10 |
| Urea | 4 to 45 |
| Carboxylic acid compound | 2 to 30 |
| Base | 0.1 to 10 |
| Hydrolate | 0.01 to 1 |

More preferred, the composition of the invention comprises the following components in percent by weight:

| Component | Amount (percent by weight) |
| --- | --- |
| C3-C6 diol | 60 to 80 |
| C8-C12 diol | 0.4 to 4 |
| Urea | 10 to 35 |
| Carboxylic acid compound | 5 to 20 |
| Base | 0.4 to 4 |
| Hydrolate | 0.02 to 0.5 |

Even more preferred, the composition of the invention comprises the following components in percent by weight:

| Component | Amount (percent by weight) |
| --- | --- |
| C3-C6 diol | 65 to 75 |
| C8-C12 diol | 0.6 to 1.5 |
| Urea | 14 to 25 |
| Carboxylic acid compound | 6 to 15 |
| Base | 0.6 to 1.5 |
| Hydrolate | 0.05 to 0.2 |

In order to obtain gel-like properties, the composition of the invention may additionally comprise one or more gelling agents. In such embodiments, the composition preferably comprises the gelling agent in an amount of at least 0.01 percent by weight, more preferably at least 0.02 percent by weight, more preferably at least 0.05 percent by weight, more preferably at least 0.1 percent by weight, more preferably at least 0.2 percent by weight, more preferably at least 0.3 percent by weight, more preferably at least 0.35 percent by weight. If the amount of gelling agent is too low, the desired gel-like properties may not be achieved to a sufficient extent. Preferably, the composition comprises gelling agents in an amount of at most 5 percent by weight, more preferably at most 2 percent by weight, more preferably at most 1 percent by weight, more preferably at most 0.8 percent by weight, more preferably at most 0.7 percent by weight, more preferably at most 0.6 percent by weight, more preferably at most 0.5 percent by weight. If the amount of gelling agent is too high, the compositions may be too viscous. Preferably, the composition comprises gelling agents in an amount of from 0.01 to 5 percent by weight, more preferably from 0.02 to 2 percent by weight, more preferably from 0.05 to 1 percent by weight, more preferably from 0.1 to 0.8 percent by weight, more preferably from 0.2 to 0.7 percent by weight, more preferably from 0.3 to 0.6 percent by weight, more preferably from 0.35 to 0.5 percent by weight.

In accordance with the invention is also a method for preparing the composition of the invention, the method comprising the following step:

a. Mixing and stirring of raw materials in order to obtain the composition of the invention.

Due to its antimicrobial and hygroscopic properties the composition of the invention is useful for treating microbial infections, in particular infections of the skin and the nails. In accordance with the present invention is therefore a composition of the invention as described above for use in the treatment of fungal, bacterial or viral infections. Preferred is a composition of the invention for treatment of diseases caused by *Candida, Pityrosporum, Trichophyton, Microsporum*, mould fungi especially *Aspergillus, Staphylococcus, Pseudomonas*, and viruses, especially herpes virus, hepatitis virus, wart virus and HIV-virus. Preferred is a composition of the invention for use in the treatment of fungal infections. Particularly preferred is a composition of the invention for use in the treatment of onychomycosis.

The composition of the invention may also be used for disinfection of skin, skin cleansing, sore and wound cleansing, as shampoos, soap, shower gels, softening preparations as well as peeling agents having antimicrobial effect, as skin preparations having antimicrobial effect intended to treat insect bites, as sun protection in combination with sunprotection agents or "after sun lotions". The composition may also be included as an additive in other cleansers and disinfecting agents to strengthen and widen the antimicrobial effects.

If the composition is used for the skin the effect works in two ways. Firstly, the infected horny layer (keratin) is removed in a mechanical way because the compositions have a peeling-effect, which reduces the microbes. These reduced microbes may subsequently be killed by the antimicrobial effect of the composition.

Due to its antimicrobial and hygroscopic effects the composition of the invention may also be used for treating or impregnating various other surfaces that not associated with the human or animal body.

Surface Treatment

The composition according to the invention may be used for treatment, cleansing and disinfecting different surfaces such as leather, wood, but also plastic, metal and ceramic materials.

Cleaning agents according to the invention differ from previously known cleaning agents and disinfecting agents containing, for example, ethyl alcohol and isopropanol, because they are both emollient and non-desiccating.

Since the composition according to the invention is not volatile as ethyl alcohol it evaporates more slowly from the surface and therefor remains on and keeps its disinfecting effect for a longer time. From the fire-risk point of view the composition has also an advantage since it is comparatively less flammable. The advantages are thus many in practical use of the invention if it is used as a cleaner for table surfaces, leather surfaces and plastic coated surfaces, e.g. dentist-chairs.

After cleaning leather and plastic an increased shine and surface finish has also been observed. Slight damage in the material has also appeared to be less obvious after treatment with the agent according to the invention. If the composition is used for wiping lacquered wood, certain types of lacquer may temporarily be dissolved on the surface. Thereafter it has been observed that previous damage in the lacquer is less obvious or invisible. These changes have been permanent. The product according to the invention may, thus, be used as an environmentally friendly and kind-to-the-skin cleansing agent and renovating agent for lacquered surfaces.

Since the composition may form an aerosol it may easily be sprayed over large areas for quicker application. Spraying may also be used for disinfection and cleansing of wrapping material, machine components, etc. or for preventing bacteria and mould attack on certain types of food-stuffs, e.g. bread, fruit, onions, as well as flower-bulbs, tobacco and animal fodder.

Another area of use for the composition according to the invention is to dissolve bacteria deposits on different surfaces or in cables or pipes.

For surface treatment of metals the composition nay also be regarded as having rust dissolving effect in the light of what is previously known. Therefore the composition is suitable as an anti-microbial effective additive in anticorrosion agents.

As an additive in lubricants and cooling mediums, for example lubricating oil and cutting fluids the antimicrobial effect of the composition may be advantageously used so that agents need not be added. By adding a buffer a suitable pH may be obtained as required.

The spraying of wood directly after sawing to inhibit the growth of surface-mould and to prevent inhalation fever in saw mill workers, is another area of use for the product according to the invention.

Impregnating

The composition according to the invention has shown itself to penetrate and be absorbed well into various materials. Treatment for preventing growth of microorganisms in deeper lying structures may be carried out by impregnating. Different materials suited for impregnating with the composition are leather; textiles, e.g. nappies, occlusive bandages, incontinence aids, tampons, sanitary towels, dressings, plasters; clothes, innersoles for shoes; wood and paper products, e.g. refresher napkins, disposable towels, waste paper, etc.

The invention includes also the possibility of chemically bonding the impregnating agent according to the invention to, for example, free carboxylic acid groups in different material or to polymers absorbed or adsorbed to such material, for example, textiles, wood or paper material. Examples of such absorbed or adsorbed polymer are alginic acid or an alginate. Treatment according to this method then gives an antimicrobial impregnation which bonds more quickly through alginic acid to textiles and wood fibers. Examples of the area of use for this antimicrobial impregnation are tampons, dressings for wounds and sores, nappies, incontinence aids and innersoles.

A gel of alginic acids or alginate to which the composition according to the invention is bonded may separately also serve as a skin and wound-care treatment without being absorbed by the textile material.

The composition may also be mixed with paints where oil is included or mixed in water-based acrylic paints to prevent mould and bacterial growth, instead of toxic anti-mould agents.

One problem when impregnating wood is that the combination according to the invention is leached by water. By adding an oil, which in itself is water repellent, this problem may be reduced to some extent. An emulsifying agent then needs to be added.

The hygroscopic effects, if used correctly, may also be an advantage since they can prevent crack-formation in wood. In the treatment of wood the impregnation with polyethylene glycols is an established method to obtain swelling of woodfibers and counter-act drying out and crack formation in the wood.

One problem which may arise with long-term treatment with polyethylene glycols is mould-formation, since polyethylene glycols do not have sufficient antimicrobial effect. Since the composition according to the invention is mixable with polyethylene glycols this new combination can prevent growth of microorganisms.

In the production of paper the risk of mould-formation is great. This is especially true of waste-paper. A further possibility of making use of the invention is, for example, to add the composition to the process water, or feed it in spray form to prevent mould-formation. Since the composition is water soluble it is easily added even to warm or cool water-systems, etc.

EXAMPLES 13 different samples have been tested for their antimicrobial effect on 4 different fungi. The samples are identified as examples A, 00, 01, 02, 03, 04, 05, 06, 07, 08, 09, 10 and 11 in the following.

Examples A and 00 comprise a carboxylic acid compound, a first diol as well as urea and a base. However, a second diol in the sense of the present invention is not in the composition. Hence, examples A and 00 are comparative examples.

Examples 01 and 03 to 08 additionally comprise a hydrolate (examples 03 to 08) or a plant extract (examples 01). However, a second diol in the sense of the present invention was not comprised. Thus, also examples 01 and 03 to 08 are comparative examples.

Examples 02 and 09 to 11 comprise a carboxylic acid compound, a first diol and a second diol in the sense of the present invention. Thus, examples 02 and 09 to 11 are examples of compositions in accordance with the present invention. Examples A, 00, 01 and 03 to 08, also examples 02 and 09 to 11 comprise urea and a base. Furthermore, examples 09 to 11 further comprise a hydrolate.

The compositions essentially consisted of the following components in percent by weight as shown in the following table 2:

TABLE 2

| Example | A | 00 | 01 | 02 | 03 | 04 | 05 | 06 | 07 | 08 | 09 | 10 | 11 |
|---|---|---|---|---|---|---|---|---|---|---|---|---|---|
| Decylene glycol | | | | 1 | | | | | | | 1 | 1 | 1 |

TABLE 2-continued

| Example | A | 00 | 01 | 02 | 03 | 04 | 05 | 06 | 07 | 08 | 09 | 10 | 11 |
|---|---|---|---|---|---|---|---|---|---|---|---|---|---|
| Urea | 20 | 18 | 18 | 18 | 18 | 18 | 18 | 18 | 18 | 18 | 18 | 18 | 18 |
| Lactic acid (90% w/w) | 10 | 9 | 9 | 9 | 9 | 9 | 9 | 9 | 9 | 9 | 9 | 9 | 9 |
| NaOH (30% w/w) | 4 | 3 | 3 | 3 | 3 | 3 | 3 | 3 | 3 | 3 | 3 | 3 | 3 |
| Thymus hydrolate | | | | | 0.05 | | | 0.1 | | | 0.1 | | |
| Oregano hydrolate | | | | | | 0.05 | | | 0.1 | | | 0.1 | |
| Mint hydrolate | | | | | | | 0.05 | | | 0.1 | | | 0.1 |
| Thymus extract | | | 5 | | | | | | | | | | |
| Propylene glyocol | ad 100 | ad 100 | ad 100 | ad 100 | ad 100 | ad 100 | ad 100 | ad 100 | ad 100 | ad 100 | ad 100 | ad 100 | ad 100 |

The term "ad 100" indicates that the examples comprised propylene glycol in such an amount that the total amount of the examples was 100 percent by weight.

Production of the example compositions is exemplarily explained in the following with regard to example 11.

In a first step 68.9 g propylene glycol (commercial name: PROPYLENE GLYCOL; supplier: SigmaAldrich), 1 g decylene glycol (commercial name: SYMCLARIOL; supplier: Symrise) and 18 g urea (commercial name: UREA; supplier: SigmaAldrich) were mixed and the mixture was heated to about 55° C. under agitation until urea was completely solubilized. Once a clear and homogeneous solution was obtained, the solution was cooled under constant agitation. Then 9 g lactic acid (commercial name: LACTIC ACID; supplier: Agrar), 3 g sodium hydroxide (commercial name: Sodium Hydroxide 30%; supplier: SigmaAldrich) and 0.1 g mint hydrolate (Mentha Rotundifolia Leaf Extract; commercial name: IDROLATO MENTA; supplier: Bionap) were added to the composition at a temperature above 30° C. and the composition was mixed until a homogeneous composition was obtained.

Example A and examples 00 to 10 were prepared accordingly.

Experiments on above described examples were conducted in two phases, namely phase A (qualitative test) and phase B (quantitative test with assessment of minimum inhibitory concentration (MIC)).

Phase A—Qualitative Test

The activity of the examples listed above was tested qualitatively against the following 4 fungi:

*Candida albicans*
*Trichophyton rubrum*
*Trichophyton mentagrophytes*
*Scopulariopsis brevicaulis*

The strains were isolated from cases of onychomycosis and were identified morphologically.

The qualitative tests were conducted in 150 mm Petri dishes containing Sabouraud agar, the surface of which was inoculated with 1 ml of fungal suspension. The dishes were left under a laminar flow hood until the suspension had been absorbed completely.

100 µl of each example were placed on 12 mm sterile discs. The discs were then placed on the surface of the agar.

The plates were then incubated at 25° C.

The zone of inhibition for each product was measured after 24 and 48 hours for *C. albicans*, after 4 and 6 days for the filamentous strains *T. mentagrophytes* and *S. brevicaulis*, and after 5 days and 6 days for the filamentous strain *T. rubrum*.

The test was carried out in two parts. During part 1, samples A, 00, 01, 02, 03, 04 and 05 were assessed. During part 2, samples 06, 07, 08, 09, 10 and 11 were assessed.

Results

The results of part 1 are shown in table 3 below. The numbers refer to the zone of inhibition of fungal growth expressed in mm. The term "st" indicates fungistatic action with "dirty" zones representing reduced fungal growth. The highest fungal inhibition achieved is shown for each fungus and each time point in bold letters.

TABLE 3

| Time | *S. brevicaulis* | | *T. mentagrophytes* | | *T. rubrum* | | *C. albicans* | |
|---|---|---|---|---|---|---|---|---|
| | 4 days | 6 days | 4 days | 6 days | 5 days | 6 days | 24 h | 48 h |
| Example A | 21.5 | 21 | 30 st | 0 | 25 | 20 | 15 | 14.5 |
| Example 00 | 25 | 24 | 35 st | 30 st | 30 | 25 st | 15 | 15 st |
| Example 01 | 24 | 23 | 40 st | 30 st | 40 | 23 | 16 | 15 st |
| Example 02 | 32 | 27 | 50 | 45 | 50 | 48 | 30 | 22 |
| Example 03 | 23 | 23 | 35 st | 35 st | 35 | 23 | 14 | 13 |
| Example 04 | 23 | 22 | 35 st | 35 st | 35 | 30 | 19 | 18 |

TABLE 3-continued

| | S. brevicaulis | | T. mentagrophytes | | T. rubrum | | C. albicans | |
|---|---|---|---|---|---|---|---|---|
| Time | 4 days | 6 days | 4 days | 6 days | 5 days | 6 days | 24 h | 48 h |
| Example 05 | 24 | 22 | 36 st | 35 st | 45 | 38 | 14 | 14 |

Example 2 was most active against all strains. Example 5 was more active against *Trichophyton mentagrophytes* as compared to examples A, 00, 01, 03 and 04, however, still less active than example 2.

In the second part, examples 06 to 11 were tested. Sample A was included in the tests as a baseline reference. The results of the second part are shown in table 4 below. The highest fungal inhibition achieved is shown for each fungus and each time point in bold letters.

TABLE 4

| | S. brevicaulis | | T. mentagrophytes | | T. rubrum | | C. albicans | |
|---|---|---|---|---|---|---|---|---|
| Time | 4 days | 6 days | 4 days | 6 days | 5 days | 6 days | 24 h | 48 h |
| Example A | 23 | 22.5 | 32.5 | 25 st | — | 33.5 | 0 | 0 |
| Example 06 | 26 | 24 | 42 | 30 st | — | 50 | 0 | 0 |
| Example 07 | 26 | 25 | 42 | 25 st | — | 30 | 0 | 0 |
| Example 08 | 26 | 24 | 42 | 30 st | — | 40 | 0 | 0 |
| Example 09 | 35 | 33 | 48 | 40 | — | 52 | 23 | 23 |
| Example 10 | 37 | 34 | 46 | 41 | — | 50 | 23 | 23 |
| Example 11 | 36 | 31 | 45 | 38 | — | 58 | 25 | 25 |

The activity of examples 09, 10 and 11 was similar, however, example 11 was most active against *C. albicans*.

In summary, part 1 and 2 of the qualitative test as shown above indicate that examples 02, 09, 10 and 11 have the greatest antifungal effect. Notably, examples 02, 09, 10 and 11 are the only examples tested that comprised a second diol in the sense of the present invention in addition to the carboxylic acid compound and the first diol.

Phase B—Quantitative Test (Assessment of Minimum Inhibitory Concentration (MIC))

Samples A, 02, 08 and 11 were tested against the same fungal strains as used for the qualitative test.

The test method was microdilution in liquid substrate. Liquid Sabouraud medium was used as the nutrient. Suspensions of fungal inoculations with a final turbidity of 0.5 DMF were prepared. Turbidity is the cloudiness or haziness of a fluid caused by large numbers of individual particles that are generally invisible to the naked eye.

The microdilutions were prepared in 24-well sterile plates, which were incubated in the dark at 35° C.

For *C. albicans*, the first measurement was performed after 24 hours, while the final MIC was measured after 48 hours. For the filamentous strains *T. mentagrophytes, T. rubrum* and *S. brevicaulis*, the measurement was performed 4 days after inoculation.

The results are shown in the following table 5. The numbers indicate the minimum concentration of the examples that demonstrated fungal growth inhibition.

TABLE 5

| | Example A | Example 02 | Example 08 | Example 11 |
|---|---|---|---|---|
| C. albicans | 7.0% | 0.4% | 7.0% | 0.3% |
| S. brevicaulis | 0.6% | 0.3% | 0.3% | 0.3% |

TABLE 5-continued

| | Example A | Example 02 | Example 08 | Example 11 |
|---|---|---|---|---|
| T. mentagrophytes | 2.5% | 0.4% | 2.0% | 0.3% |
| T. rubrum | 2.5% | 0.4% | 2.0% | 0.4% |

The results demonstrate that example 11 is most effective, closely followed by example 02.

In summary, the experiments as shown herein indicate that compositions according to the present invention comprising a carboxylic acid compound as well as a small first diol and a larger second diol have improved antifungal properties as compared to compositions that do not comprise a second diol.

Moreover, it was found by the inventors that example 11 showed the same MIC when the experiment was repeated one week later, in contrast to example 02 whose antifungal performance was impaired. Notably, examples 02 and 11 differ only by the presence of mint hydrolate in example 11. Thus, even though both example 02 and example 11 show excellent antifungal effects, it seems that presence of hydrolates, in particular of mint hydrolate, improves the storability of the compositions.

It should be noted that the examples described above were provided with gel-like properties by addition of polyquaternium-10 in an amount of about 0.4 percent by weight without influencing the antifungal effects. Polyquaternium- 10 was added to the compositions described above under agitation and mixing until the polymer was entirely dispersed in the composition and a clear gel was obtained.

The invention claimed is:

1. A composition comprising,
   about 9 wt. % of lactic acid,
   about 1.0 wt. % decylene glycol,
   about 18 wt. % urea,
   about 3 wt. % NaOH,
   about 0.05-0.1 wt. % of a hydrolate selected from the group consisting of mint hydrolate, oregano hydrolate, and thymus hydrolate;
   and an amount of propylene glycol sufficient to bring the composition to 100 wt %.

2. The composition of claim 1, wherein the hydrolate is mint hydrolate.

3. The composition of claim 1, wherein the hydrolate is oregano hydrolate.

4. The composition of claim 1, wherein the hydrolate is thymus hydrolate.

* * * * *